United States Patent [19]
Min et al.

[11] Patent Number: 6,037,301
[45] Date of Patent: Mar. 14, 2000

[54] AMORPHOUS ALLOY CATALYST CONTAINING BORON, ITS PREPARATION AND USE

[75] Inventors: Enze Min, Beijing; Jingfa Deng, Shanghai; Aizeng Ma; Wanzhen Lu, both of Beijing, all of China

[73] Assignees: China Petro-Chemical Corporation; Research Institute of Petroleum Processing Sinopec; Fudan University, all of, China

[21] Appl. No.: 09/061,081

[22] Filed: Apr. 15, 1998

[30] Foreign Application Priority Data

Apr. 24, 1997 [CN] China ................................. 97104064

[51] Int. Cl.$^7$ ................................................. B01J 21/02
[52] U.S. Cl. ................................ 502/207; 502/202
[58] Field of Search ................................ 502/202, 207

[56] References Cited

U.S. PATENT DOCUMENTS 4,602,000  7/1986  Dupin et al. ............................ 502/335

FOREIGN PATENT DOCUMENTS 1073726A  6/1993  China .

OTHER PUBLICATIONS

Applied Catalysis, 37 (1988) 339–343, published by Elsevier Science Publishers B.V. Amsterdam no month available.

Journal of Catalysis150, 434–438 (1994) by Academic Press, Inc. no month available.

Catalytic Properties of Amorphous Ni–B Alloy for Hydrogenation, (1994), publisher unknown, Li Bingshi, Yang Jun and Deng Jingfa no month available.

Journal of Physical Chemistry (1993) 97, 8507–8511, Reactions of Bivalent Metal Ions with Borohydride in Aqueous Solution for the Preparation of Ultrafine Amorphous Alloy Particles no month available.

ACTA Physico–Chimica Sinica, vol. 9, No. 3 (Jun. 1993) considered to the extent of English abstracts.

*Primary Examiner*—Elizabeth D. Wood
*Attorney, Agent, or Firm*—Jones & Askew, LLP

[57] ABSTRACT

The present invention discloses an amorphous alloy catalyst containing boron, which is composed of a porous carrier, a Q-B amorphous alloy, and a metal additive (M), the content of Q-B amorphous alloy together with metal additive is from 0.1 to 60 wt %, based on the total weight of the catalyst, in which the atomic ratio (Q+M)/B is 0.5–10, and the Q/M atomic ratio is 0.1–1000; wherein Q represents an metal selected from group VIII and B represents boron; and said metal additive (M) refers to those one or more metal elements which can be reduced to its/their elemental states from the corresponding salts by a solution containing $BH_4^-$ with the exception that M is not the one which is used as Q. Said catalyst exhibits high catalytic hydrogenation activity.

21 Claims, 6 Drawing Sheets

AMORPHOUS ALLOY CATALYST CONTAINING BORON, ITS PREPARATION AND USE

FIELD OF THE INVENTION

The present invention relates to an amorphous alloy catalyst and its preparation and use. In more detail, the invention relates to an amorphous alloy catalyst containing a metal (Q) selected from group VIII of the periodic table, and boron, and to its preparation and use.

BACKGROUND OF THE INVENTION

The following two problems need be overcome during the development of the amorphous alloy catalysts. One problem concerns how to increase the surface area of the amorphous alloy catalyst, so that its catalytic activity can be improved. The other problem concerns how to keep the catalyst in its amorphous state, i.e. how to enhance the thermal stability of the amorphous alloy catalyst. Numerous previous attempts have been directed toward addressing these problems.

In CN1,073,726A, an alloy containing Al, rare earth elements (RE), P, and Ni or Co or Fe was prepared by rapid quenching techniques. By alkaline leaching Al from the alloy with NaOH, a Ni/Co/Fe-RE-P amorphous alloy catalyst with high surface area up to 50–130 m²/g was obtained. Its hydrogenation activity was higher than that of Raney Ni, which is widely used in industry. Such a catalyst exhibited the highest reactivity among all the prior art amorphous alloy catalysts reported thus far.

An ultra-fine Ni-B amorphous alloy catalyst was reported in J. Catal. 150 (1994) 434–438. This catalyst was prepared by adding a 2.5 M aqueous $KBH_4$ solution dropwise at 25° C. to an alcoholic nickel acetate solution at a concentration of 0.1 M with stirring. The resulted Ni-B catalyst was then washed with 6 ml of 8 M $NH_3 \cdot H_2O$ and subsequently with a large amount of distilled water. However, ultra-fine Ni-B amorphous alloy particles obtained in this manner exhibited poor thermal stability, although their surface area was determined as high as 29.7 m²/g.

A Ni-P amorphous alloy catalyst deposited on silica was reported in Appl. Catal. 37 (1988) 339–343. This catalyst was prepared by chemical plating to deposit Ni and P onto a silica support. Such a supported Ni-P amorphous alloy catalyst exhibited not only a high surface area (up to 85 m²/g), but also superior thermal stability over the corresponding unsupported amorphous alloy catalysts.

According to the results concerning the mechanism of formation of the Ni-B amorphous alloy obtained by chemical reduction, as reported in J. Phys. Chem. 97 (1993) 8504–8511, the reaction between the metal ion $M^{2+}$ and $BH_4^-$ in an aqueous solution follows the three steps given below:

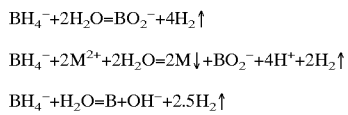

$BH_4^- + 2H_2O = BO_2^- + 4H_2\uparrow$ $BH_4^- + 2M^{2+} + 2H_2O = 2M\downarrow + BO_2^- + 4H^+ + 2H_2\uparrow$ $BH_4^- + H_2O = B + OH^- + 2.5H_2\uparrow$ Since all of these three reactions proceed very rapidly, efficient deposition of the resulting Ni-B amorphous alloy on the support could not be guaranteed when chemical plating is carried out by mechanically mixing the support and the plating solution, nor could the homogeneous distribution of Ni-B amorphous alloy on the support be assured. Therefore, the deposition of a Ni-B amorphous alloy on the support becomes a difficult problem in this field.

Another way to improve the reactivity and/or thermal stability of the catalysts is achieved by introducing metal additives into an amorphous alloy, which has been reported widely elsewhere.

It was reported by Baoning Zong et al. in Physica Chinica Acta 9 (1993) 325 that by introducing groups IIIB or rare earth elements (abbreviated RE), such as Y, Ce and Sm, the resulted unsupported Ni-RE-P amorphous alloy catalysts exhibited a much better thermal stability over the corresponding Ni-P amorphous alloy catalyst. Similar results were also obtained by introducing La instead of the above rare earth elements, as reported in J. Chem. Soc., Faraday Trans. I 82 (1986) 702.

The effects of metal additives, such as Pd, Co, Cu, or Fe, on the hydrogenation properties of the unsupported Ni-B amorphous alloy catalysts were studied by Bingshi Li, as reported in Petrochemical Technology 23 (1994) 791. These results demonstrated that the addition of Pd could promote the activity of the Ni-B amorphous alloy catalyst for cyclopentadiene hydrogenation, while other metal additives including Co, Cu and Fe cause the reduction of hydrogenation activity.

Up to now, although various attempts have been made to improve both the reactivity and thermal stability of the amorphous alloy catalysts, unfortunately, no catalysts reported thus far can match the Ni-RE-P amorphous alloy catalyst with respect to its high surface area as described in CN 1,073,726A, or with respect to their catalytic activity.

PURPOSE OF THE INVENTION

One object of the invention is to provide an amorphous alloy catalyst containing a metal selected from the group VIII of the periodic table, and boron, which exhibits higher catalytic activity than that of the existing catalysts.

Another object of the invention is to provide a process for the preparation of such an amorphous alloy catalyst.

A further another object of the invention is the use of such an amorphous alloy catalyst.

SUMMARY OF THE INVENTION

The catalyst according to the present invention is composed of a porous carrier, a Q-B amorphous alloy and a metal additive (M), the content of the Q-B amorphous alloy together with metal additive is from 0.1 to 60 wt %, based on the total weight of the catalyst, in which the atomic ratio (Q+M)/B is 0.5–10, and the atomic ratio Q/M is 0.1–1000; wherein Q represents a metal selected from group VIII of the periodic system of the elements and B represents boron; and said metal additive (M) refers to one or more metal elements which can be reduced into its/their elemental states from the corresponding salts by a solution containing $BH_4^-$ with the exception that M is not the metal which is used as Q.

The process for preparation of said catalyst comprises contacting a porous carrier containing Q and a metal additive (M) with a solution containing $BH_4^-$ at a molar concentration of between 0.5–10 M, in a initial molar ratio of B/(Q+M) being from 0.1 to 10 M and a initial molar ratio of Q/M in said porous carrier being from 0.1 to 80 M, at a temperature ranging from the melting point of the solution to 100° C.

The use of said catalyst refers to their use in the hydrogenation of compounds having unsaturated functional groups.

DETAILED DESCRIPTION OF THE INVENTION

According to the catalyst of the present invention, the total content of the Q-B amorphous alloy together with metal additive (M) is from 0.1 to 60 wt %, preferably 0.1–40 wt %, and most preferably 0.1–30 wt %.

The preferable atomic ratio (Q+M)/B is from 1 to 8, the preferable atomic ratio Q/M is 0.5–100, and the optimum atomic ratio is 0.5–25.

Q described in the present invention represents a metal selected from group VIII of the periodic table. In other words, Q refers to Ni, Fe, Co, Ru, Rh, Pd, Os, Ir or Pt. Among these metals, Ni, Ru or Pd is preferable, and Ni is most preferable.

The porous carrier described in the present invention refers to porous carrier material without oxidizability. Preferable porous carrier material is selected from porous inorganic oxide, active carbon, zeolite, molecular sieve or any mixtures thereof. Said porous inorganic oxide refers to one or more solid oxides of those elements in group IIA of the periodic table, IIIA and IVA of the periodic table, among which, a single oxide or a mixture of oxides from the group $SiO_2$, $Al_2O_3$, MgO, and CaO are preferable. Said zeolite and molecular sieve refer to a single one or a mixture of various kinds of aluminosilicate zeolites and molecular sieves containing heteroatoms, such as A-type zeolites, X-type zeolites, Y-type zeolites, ZSM series zeolites, Beta zeolites, Ω zeolite, P-Al molecular sieves, Ti-Si molecular sieves, etc. The preferred porous carrier is $SiO_2$, $Al_2O_3$ or active carbon.

The metal additive (M) described in the present invention refers to one or more metal elements which can be reduced to their elemental states from their corresponding salts by a solution containing $BH_4^-$ with the exception that M is not the one which is used as Q. The preferable metal additive (M) is selected from one or several metal elements in the groups IVA, IB, IIB, IIIB, VIB, VIIB, VIII, and the Lanthanides and Actinides, with the exception that M is not the one which is used as Q. This means that if Q is Ni, the metal additive can be selected from not only at least one metal element in groups IVA, IB, IIB, IIIB, VIB, VIIB, and the Lanthanides and Actinides, but also at least one metal element in group VIII except for Ni itself. If Q is Pd, the metal additive can be selected from not only at least one metal element in the groups IVA, IB, IIB, IIIB, VIB, VIIB, and the Lanthanides and Actinides, but also at least one metal element in group VIII except for Pd itself. The more preferable metal additive (M) is selected from one or more metal elements comprising Fe, Co, Ni, Ru, Rh, Pd, Os, Ir, Pt, Zn, Cr, Mn, Cu, Ag, Mo, W, Sn, and the Lanthanides and Actinides. The commonly used metal additive is selected from one or several metal elements comprising Cu, Zn, Mn, Ag, Mo, W, La, Ce, Sm, Nd, Gd, Fe, Co, Ni, Ru, Rh, Pd, Os, Ir, and Pt. The most commonly used metal additive is selected from one or several metal elements comprising Fe, Co, Cu, Zn, Mn, Ag, Mo, W, Pd, Ru, Ir, La, Ce, Sm, Nd, and Gd.

According to the catalyst of the present invention, its surface area could vary in range of between 10 and 1000 $m^2/g$, preferably between 100 and 1000 $m^2/g$, depending on the surface area of the carrier.

According to the catalyst of the present invention, all the active Q species are present in an amorphous state. The metal additive (M) may be present in the following two states: (1) By alloying with Q-B, M can be present in the form of Q-M-B amorphous alloy, which is confirmed by the X-ray diffraction (XRD) patterns with a CuKα target. As shown in FIG. 1(1), a broad peak around 2θ=45° is observed, indicating the typical amorphous character of this kind of catalyst; (2) The metal additive (M) may also be present in a polycrystalline phase together with the Q-B amorphous alloy. In this case, the polycrystalline diffractional peaks of such a metal additive could be observed by the XRD patterns, as shown in FIG. 1(2). In some cases, the broad peak resulting from the Q-M-B amorphous alloy and/or the diffractional peaks from the metal additive M polycrystalline phase may be covered by the overlapping diffractional peaks arising from the carrier, as shown in FIGS. 2, 3 and 4.

The detailed procedures for the preparation of the catalyst provided in the present invention are described as follows:

(1) The porous carrier is impregnated either with the mixture solution containing the desired amount of soluble salts of Q and of a metal additive M, or with one salt solution first, and then, after being dried, with another salt solution. The porous carrier containing Q and the metal additive M obtained in this fashion is then dried at a temperature ranging from room temperature to 200°.

(2) At a temperature range from the melting point of the solution to 100° C., the porous carrier containing Q and the metal additive M is contacted with a solution containing $BH_4^-$ at a concentration between 0.5–10 M, in which the initial molar ratio between B and (Q+M) absorbed in the porous carrier is adjusted to 0.1 to 10.

(3) The solid product is then washed with distilled water until it is free from acidic ions.

Said porous carrier containing Q and the metal additive (M) can also be obtained commercially, or obtained by impregnating the commercially available porous carriers containing Q (or metal additive) with the salt solution containing metal additive (or Q). Impregnation with the salts of Q and/or the metal additive can be conducted using those impregnation methods which are widely used in catalyst preparation, with impregnation up to saturation being most preferable. Other methods, such as mechanical mixing or ion exchange techniques, could be employed to deposit Q and/or the metal additive (M) into the carrier, especially when the zeolites or molecular sieves or other exchangeable carriers are used as porous carriers.

The Q salt solution described here refers to either an aqueous or an alcoholic solution. Said Q salt can be selected from one or more of the Q salts which are soluble in water or alcohol, such as the chlorides of Ni, Co, Fe, Ru, Rh, Pd, Os, Ir, Pt, soluble nickel carboxylate, soluble cobalt carboxylate, $FeSO_4$, $Pd(NH_3)_4Cl_2$, $Pt(NH_3)_4Cl_2$, $H_2PtCl_4$, etc.

The salt solution of metal additive (M) described here refers to either an aqueous or an alcoholic solution. Said salt of the metal additive can be selected from one or more of the M salts which are soluble in water or in ethanol.

Preferably, the described porous carrier containing Q and the metal additive (M) is pre-dried at 90–200°.

The commonly used solution containing $BH_4^-$ ions is an aqueous $BH_4^-$ solution. The precursor of $BH_4^-$ ions is obtained from $KBH_4$ or $NaBH_4$ or their mixture. The optimum B/(Q+M) initial atomic ratio is 1–4. The preferable Q/M atomic ratio is 0.5–20.

The contact between the porous carrier containing Q plus the metal additive (M) and $BH_4^-$ solution could be achieved by either directly mixing, or by adding the $BH_4^-$ solution slowly and dropwise to the designated carrier, the latter method being preferable.

Although the contact and the reaction between the porous carriers containing Q and the metal additive (M) and $BH_4^-$ solution could also be performed at a temperature higher than 100° C., the temperature is usually controlled at a temperature ranging from just above the melting point to 100° C. for saving energy. The optimum reaction temperature is in range of from room temperature to 50° C.

The catalyst provided by the present invention can be employed in the hydrogenation process of compounds containing unsaturated functional groups, wherein said compounds may be alkenes, alkynes, aromatic hydrocarbons, nitro-compounds, keto-compounds, carboxyl compounds or nitriles. Hydrogenation refers to saturated or selective hydrogenation, especially the selective hydrogenation of trace ethyne in ethylene. The hydrogenation conditions employed are those commonly used in each of the respective hydrogenation reactions.

The catalyst of the present invention exhibits superior hydrogenation activities over all of the prior art amorphous alloy catalysts reported so far. For example, the catalytic activities of (1) the inventive amorphous alloy catalyst with 3.57 wt % Ni, 0.89 wt % Co and 0.24 wt % B supported on $SiO_2$; (2) the Ni-La-P amorphous alloy catalyst with high surface area described in CN 1073726A; and (3) the traditional polycrystalline Ni catalyst with 5 wt % Ni, were each tested for their styrene hydrogenation activity at 60° C. The conversions of styrene over each of those catalysts were: (1) 18.63 wt %, (2) 16.60 wt %, and (3) only 0.1 wt %, respectively. These results demonstrate that the reactivity of the catalyst of the present invention is 186 times higher than that of the traditional polycrystalline nickel catalyst. Its reactivity is even higher than that of the Ni-La-P amorphous alloy catalyst with a high surface area, which is the highest activity amorphous catalyst among those obtained according to prior art techniques. It is also demonstrated that the content of the active metal in the catalyst of the present invention is in a much more finely divided state and a more homogeneously distributed state than that in the Ni-La-P catalyst, since Ni-loading in the Ni-Co-B/carrier catalyst of the present invention is only 3.57 wt %, and the total content of Ni and Co is only 4.46 wt %, while the Ni-loading in Ni-La-P catalyst known from prior art is up to 87.4 wt %. These results indicate that the present Ni-M-B/carrier catalyst is an effective catalyst with low Ni-loading, displaying superiority over catalysts known from prior art techniques. For example, the following catalysts of the present invention: $C_1$ (3.64 wt % Ni, 1.18 wt % Cu and 0.22 wt % B deposited on $SiO_2$), $C_4$ (3.10 wt % Ni, 0.89 wt % Mn and 0.14 wt % B deposited on $SiO_2$), $C_5$ (2.79 wt % Ni, 1.80 wt % Zn and 0.13 wt % B deposited on $SiO_2$), $C_{12}$ (3.50 wt % Ni, 2.50 wt % W and 0.17 wt % B deposited on $SiO_2$), and $C_{13}$ (4.17 wt % Ni, 2.22 wt % Ag and 0.24 wt % B deposited on $SiO_2$), were used as catalysts during the selective hydrogenation of trace ethyne in ethylene at T=110° C., P=10.0 MPa, and the space velocity (gas volume)=9000 $hour^{-1}$. The results show that the activity of each of those catalysts is higher than both the Ni-La-P amorphous alloy catalyst with a high surface area and the polycrystalline nickel catalyst, as shown in FIG. 5.

The surface area of the catalyst of the present invention could be adjusted freely by choosing a different surface area of the carrier, by which a very high surface area up to 1000 $m^2$/g of the catalyst could be obtained. On the contrary, the surface area of Ni-RE-P amorphous alloy catalysts reported as the highest so far is only 130 $m^2$/g.

The catalyst of the present invention exhibits excellent thermal stability. Its maximum crystallization temperature is higher than 350° C., which is 9.6° C. higher than the ultra-fine Ni-B amorphous alloy (its highest crystallization temperature is 341.42° C.). Their thermal stability could be further improved by introducing those metal additives (M) which have a larger atomic size and could form an amorphous alloy with Ni-B. For example, the highest crystallization temperature of Ni-B amorphous alloys with Zn, Mo, and W metal additives, could reach 411° C., 429° C., and 430° C., respectively.

Instead of the traditional technological route for preparing Ni-B amorphous alloy by $BH_4^-$ reduction of nickel species in solution, the catalyst of the present invention is prepared by pre-dispersing Q and metal additive (M) into the porous carrier, then reducing Q and M with a $BH_4^-$ solution. In the first instance, the resulted Q-M-B amorphous alloy or the mixture of the amorphous alloy and polycrystalline metal can be deposited into the porous carrier. In the latter case, their distribution in the carrier is more homogeneous, which is superior to the prior art techniques such as the chemical plating.

EXAMPLES

The following examples are given only for the purpose of a detailed explanation of the present invention. It should be stressed that the present invention is not limited by these examples.

Examples 1–22

(1) Carriers

Carrier 1 (No. $Z_1$) refers to silica gel with a large pore size which is available from Qingdao Haiyang Chemical and Engineering Company, China. Carrier 2 (No. $Z_2$) refers to silica gel with a small pore size which is available from the same company as mentioned above. Carrier 3 (No. $Z_3$) refers to the $\delta$-$Al_2O_3$ which is prepared by calcining spherical $Al_2O_3$ at 900° C. for 4 hours, which itself is used as the carrier for CB-8 catalyst and is available from Changling Catalyst Company, China. Carrier 4 (No. $Z_4$) refers to $\gamma$-$Al_2O_3$ which is prepared by calcining spherical $Al_2O_3$ at 650° C. for 4 hours, which is also used as the carrier of CB-8 catalyst and is available from Changling Catalyst Company, China. The physiochemical properties of these four carriers ($Z_1$–$Z_4$) are summarized in Table 1, in which the crystalline phases are determined by XRD, the surface area and pore volume are determined by BET nitrogen adsorption at low temperature (Micromeristics ASAP 2400, U.S.A).

TABLE 1

| Carrier No. | Type | $S_{BET}$, m²/g | $V_{pore}$, ml/g | Cryst. Phase |
| --- | --- | --- | --- | --- |
| $Z_1$ | $SiO_2$ | 401 | 0.95 | Amorphous |
| $Z_2$ | $SiO_2$ | 672 | 0.39 | Amorphous |
| $Z_3$ | $Al_2O_3$ | 124 | 0.49 | δ |
| $Z_4$ | $Al_2O_3$ | 153 | 0.47 | γ |

Figure 1:
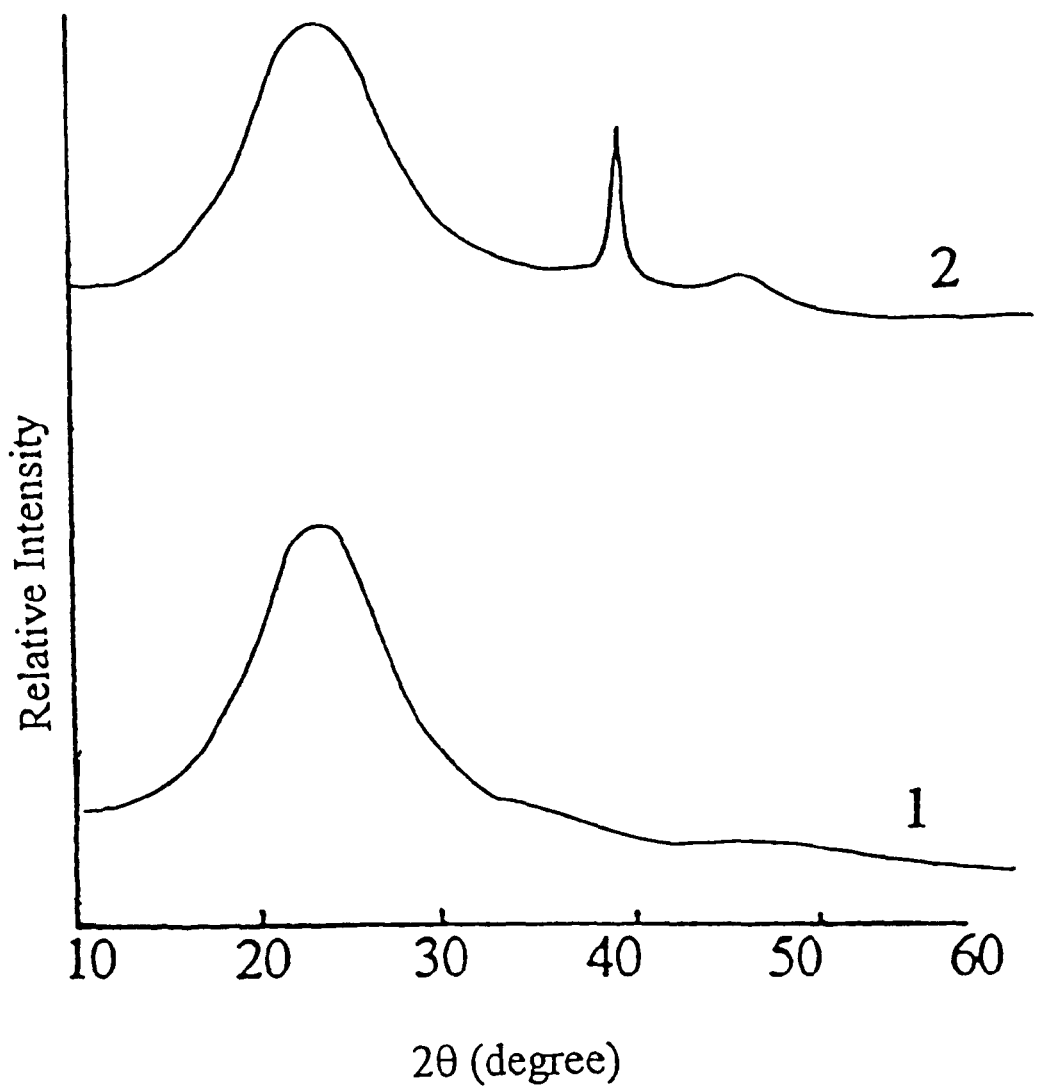
FIG. 1 shows the XRD patterns of the amorphous alloy catalysts according to the present invention using $SiO_2$ as the carrier.
Figure 2:
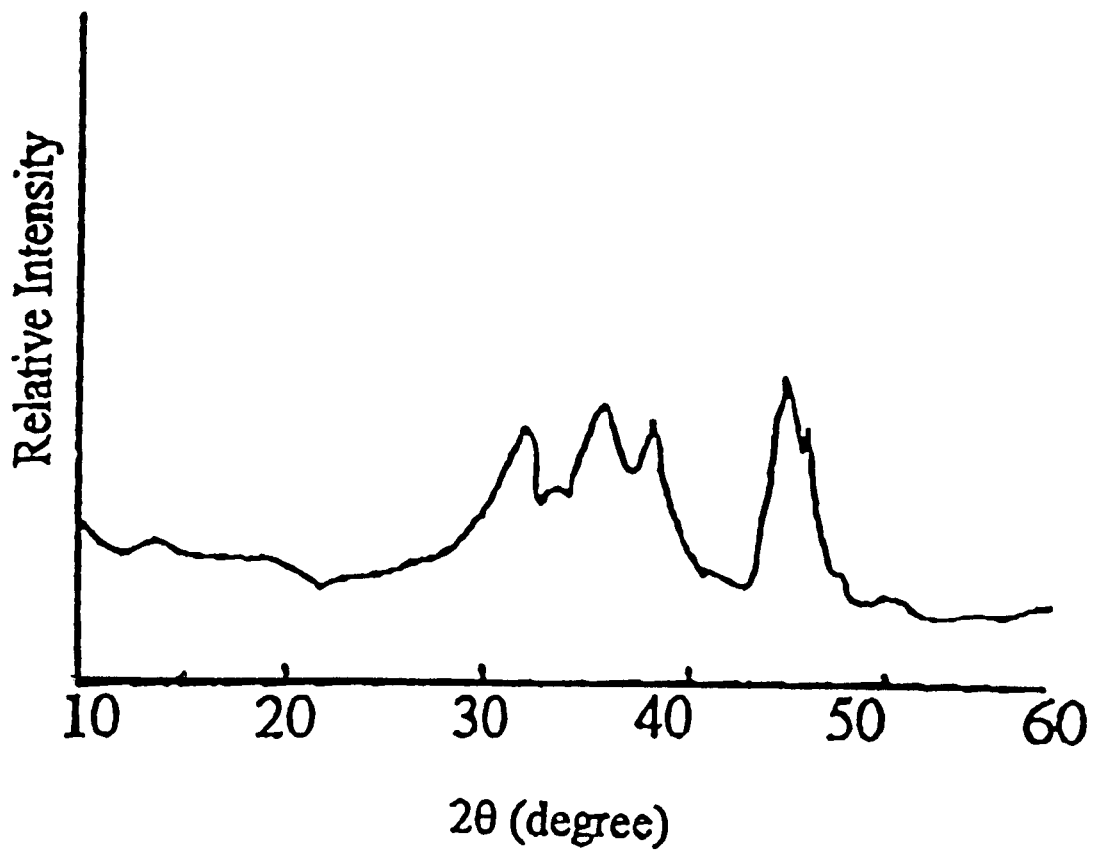
FIG. 2 shows the XRD patterns of the amorphous alloy catalysts according to the present invention using $\delta$-$Al_2O_3$ as the carrier.
Figure 3:
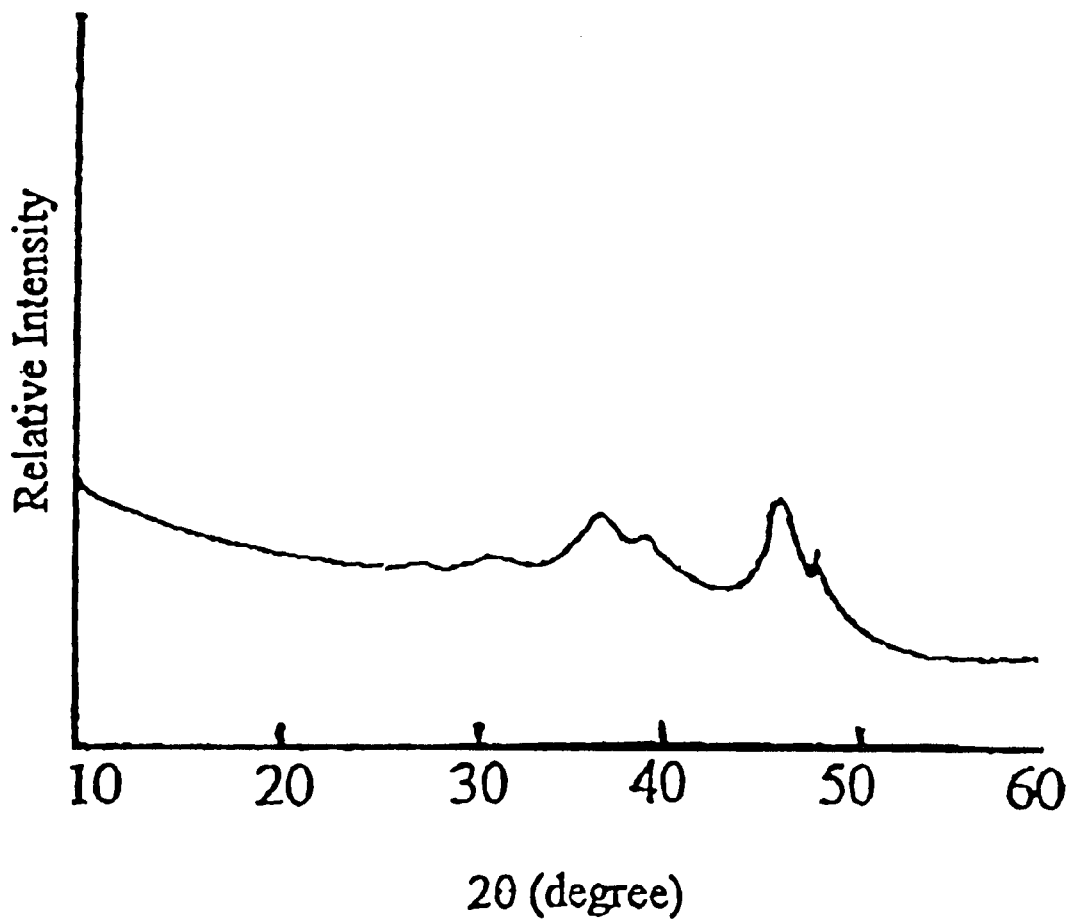
FIG. 3 shows the XRD patterns of the amorphous alloy catalysts according to the present invention using $\gamma$-$Al_2O_3$ as the carrier.

(2) Catalyst Preparation (a) The amounts of each of the above mentioned carriers ($Z_1$–$Z_4$) listed in Table 2 are dried at 120° C. The amount of $NiAc_2.4H_2O$ (where Ac is acetate) listed in Table 2 is mixed with the amounts of $CuSO_4.5H_2O$, $FeSO_4.7H_2O$, $CoAc_2.4H_2O$, $MnCl_2.4H_2O$, $ZnCl_2$, or $Na_2MoO_4.2H_2O$, respectively, also listed in Table 2. The amount of distilled water indicated in Table 2 is then added to the mixture to prepare the appropriate immersing solution mixtures, which are then used for immersing the different carriers. After the immersion step, the porous carriers containing Ni and the different metal additives are obtained by drying the carriers at 120° C. An aqueous solution of $KBH_4$ is prepared, using the amount of $KBH_4$ provided in Table 2, and this solution is then added dropwise at room temperature to the carriers obtained above. The reduction reaction is initiated immediately with the release of large amounts of $H_2$ gas being observed. After completion of the reaction, as indicated when no more $H_2$ is evolved, the solid products obtained are washed free from acidic ions with distilled water to provide the catalysts of the present invention. These catalysts are numbered from $C_1$ to $C_{10}$, corresponding to experiment numbers 1 to 10 of Table 2. Table 2 shows the quantities of all the materials used during the preparation. The content of B, Ni and metal additives as well as the surface area of catalysts $C_1$ to $C_{10}$ are provided in Table 6. The XRD patterns of the catalysts $C_1$–$C_7$ are shown in FIG. 1(1), the XRD patterns of catalysts $C_8$ and $C_9$ are shown in FIG. 2, and the XRD pattern of catalyst $C_{10}$ is shown in FIG. 3.

The B, Ni and metal additive contents in the catalysts are determined by ICP on a Jarrel-Ash 1000 after the sample is dissolved by a microwave method. The XRD is performed on a D/MAX-3A X-ray diffractometer using CuKα radiation, 40 kV tube voltage, and 35 mA tube electric current. The measurements of the surface area of each catalyst are performed by the same method described above.

As indicated from the XRD patterns of catalysts $C_1$–$C_{10}$, the metal additive (M) may form amorphous alloys with Ni-B, i.e. the metal additive (M) may be present in the form of Ni-M-B amorphous alloy in the inventive catalysts, since only one broad peak around 2θ=45° is observed. However, when δ-$Al_2O_3$ or γ-$Al_2O_3$ are used as the carrier, the broad peaks around 2θ=45° are obscured by the diffraction peaks of δ-$Al_2O_3$ or γ-$Al_2O_3$ at the corresponding position.

(b) The amounts of carriers $Z_1$ and $Z_3$ listed in Table 3 are dried at 120° C. Next, the weight of $NiAc_2.4H_2O$ indicated in Table 3 is dissolved in the appropriate amount of distilled water, also indicated in Table 3. The indicated weight of $Na_2MoO_4.2H_2O$, $Na_2WO_4.2H_2O$, and $AgNO_3$ are then dissolved in the amount of distilled water from Table 3 to prepare $Na_2MoO_4$, $Na_2WO_4$, and $AgNO_3$ aqueous solutions, respectively. The above carriers are pre-impregnated with $NiAc_2$ aqueous solution. After being dried at 120° C., the Ni-impregnated carrier is further impregnated with $Na_2MoO_4$, $Na_2WO_4$, and $AgNO_3$ aqueous solutions, respectively. The remaining preparation steps are the same as those described above in (a). The resulted catalysts according to the present invention are numbered $C_{11}$ to $C_{14}$ to correspond to experiment numbers 11 to 14 of Table 3. Table 3 lists the quantities of all the materials used during these preparations. The contents of B, Ni and metal additives and the surface area of the catalysts $C_{11}$ to $C_{14}$ are provided in Table 6. The XRD patterns corresponding to catalyst $C_{11}$ and $C_{12}$ are shown in FIG. 1(1), the XRD pattern corresponding to catalyst $C_{13}$ is shown in FIG. 1(2), and the XRD pattern corresponding to catalyst $C_{14}$ is shown in FIG. 2. The measurements of the content of Ni, B and metal additives, the surface area, and the XRD patterns were performed using the same methods as those described in (a) above.

As indicated from the XRD pattern of catalyst $C_{13}$, the metal additive in the catalysts of the present invention can be present in the form of Ni-B amorphous alloy and additive metal polycrystalline phases, such as polycrystalline Ag. The XRD pattern shows the appearance of diffractional peaks of polycrystalline metal. In FIG. 1(2), the sharp peak at 2θ=38° corresponds to the polycrystalline Ag diffraction peak.

(c) The amount of carrier $Z_3$ indicated in Table 4 is dried at 120° C. The amounts of both $NiAc_2.4H_2O$ and $CuSO_4.5H_2O$ provided in Table 4 are then dissolved in the amount of distilled water from Table 4 to prepare a mixed aqueous solution containing both $NiAc_2$ and $CuSO_4$. An aqueous $AgNO_3$ solution is prepared by dissolving the amounts of $AgNO_3$ in the indicated amount of distilled water from Table 4. The above carriers are pre-impregnated with the different amounts of $NiAc_2$ and $CuSO_4$ in the mixed aqueous solutions. After the pre-impregnation step, the resulting carriers are dried at 120° C. These pre-impregnated carriers containing different amounts of Ni and Cu are further impregnated with the $AgNO_3$ aqueous solution, prepared as indicated in Table 4, and then dried at 120° C. again. The further catalyst preparation steps are the same as those in (a), and the resulted catalysts according to the present invention are numbered as $C_{15}$ to $C_{20}$, corresponding to experiment numbers 15 to 20 in Table 4. Table 4 lists the quantities of all the materials used during the preparation. The contents of B, Ni and metal additives, and the surface area of the catalysts $C_{15}$ to $C_{20}$ are given in Table 6. The XRD patterns corresponding to catalysts $C_{15}$ to $C_{20}$ are shown in FIG. 2. The measurement of the contents of Ni, B and metal additives, the surface area, and the XRD patterns are performed using the same methods as those described in (a).

(d) The amount of carrier $Z_1$ indicated in Table 5 is dried at 120° C. The amounts of $NiAc_2.4H_2O$, $Na_2MoO_4.2H_2O$ and $Na_2WO_4.2H_2O$ indicated in Table 5 are dissolved in the appropriate amount of distilled water listed in Table 5, to prepare separate aqueous solutions of these metals. The above carrier is pre-impregnated with $Na_2MoO_4.2H_2O$ or $Na_2WO_4.2H_2O$ aqueous solution. After being dried at 120° C., the pre-impregnated carriers containing Mo or W are both further impregnated with the $NiAc_2$ aqueous solution, respectively. The remaining preparation steps are the same as those in (a), and the resulting catalysts according to the present invention are numbered as $C_{21}$ to $C_{22}$, corresponding to experiment numbers 21 and 22 of Table 5. Table 5 lists the quantities of all the materials used during the preparations. The content of B, Ni and metal additives and the surface area of catalysts $C_{21}$ to $C_{22}$ are provided in Table 6. The XRD patterns corresponding to catalyst $C_{21}$ and $C_{22}$ are shown in FIG. 1(1). The measurements of the content of Ni, B and metal additives, the surface area measurements, and the XRD patterns are performed using the same methods as those described above in (a).

TABLE 2

| Exp. No. | Carrier Type | W (g) | $W^a_{NiAc_2.4H_2O}$ (g) | Mixed solution of NiAc₂ and M salt $M^b$ salt | $W_M$ (g) | $W_{H_2O}$ (g) | $KBH_4$ solution $W_{KBH_4}$ (g) | $W_{H_2O}$ (g) | Initial atomic ratio Ni/M | Initial atomic ratio B/(Ni + M) |
|---|---|---|---|---|---|---|---|---|---|---|
| 1 | $Z_1$ | 5.00 | 1.00 | $CuSO_4.5H_2O$ | 0.25 | 9.00 | 0.56 | 12.00 | 4.01 | 2.07 |
| 2 | $Z_1$ | 5.00 | 1.00 | $FeSO_4.7H_2O$ | 0.28 | 9.00 | 0.56 | 12.00 | 3.99 | 2.07 |
| 3 | $Z_1$ | 5.00 | 1.00 | $CoAc_2.4H_2O$ | 0.25 | 9.00 | 0.56 | 12.00 | 4.00 | 2.07 |
| 4 | $Z_1$ | 5.00 | 1.00 | $MnCl_2.4H_2O$ | 0.20 | 9.00 | 0.56 | 12.00 | 3.98 | 2.06 |
| 5 | $Z_1$ | 5.00 | 1.00 | $ZnCl_2$ | 0.15 | 9.00 | 0.56 | 12.00 | 3.65 | 2.03 |
| 6 | $Z_1$ | 5.00 | 1.00 | $Na_2MoO_4.2H_2O$ | 0.25 | 9.00 | 0.79 | 12.00 | 3.89 | 2.05 |
| 7 | $Z_2$ | 5.00 | 1.00 | $CuSO_4.5H_2O$ | 0.25 | 6.00 | 0.56 | 8.00 | 4.01 | 2.07 |
| 8 | $Z_3$ | 5.00 | 1.00 | $CuSO_4.5H_2O$ | 0.25 | 5.00 | 0.56 | 7.00 | 4.01 | 2.07 |
| 9 | $Z_3$ | 5.00 | 1.00 | $ZnCl_2$ | 0.15 | 5.00 | 0.56 | 7.00 | 3.65 | 2.03 |
| 10 | $Z_4$ | 5.00 | 1.00 | $CuSO_4.5H_2O$ | 0.25 | 5.00 | 0.56 | 7.00 | 4.01 | 2.07 |

$^a$W means the weight of different materials
$^b$M means metal additives, the same hereafter

TABLE 3

| Exp. No. | Carrier Type | W (g) | $NiAc_2$ Solution $W_{NiAc_2.4H_2O}$ (g) | $W_{H_2O}$ (g) | Solution of metal additive salt M salt | $W_M$ (g) | $W_{H_2O}$ (g) | $KBH_4$ solution $W_{KBH_4}$ (g) | $W_{H_2O}$ (g) | Initial atomic ratio Ni/M | Initial atomic ratio B/(Ni + M) |
|---|---|---|---|---|---|---|---|---|---|---|---|
| 11 | $Z_1$ | 5.00 | 1.00 | 9.00 | $Na_2MoO_4.2H_2O$ | 0.25 | 9.00 | 0.79 | 12.00 | 3.89 | 2.89 |
| 12 | $Z_1$ | 5.00 | 1.00 | 9.00 | $Na_2WoO_4.2H_2O$ | 0.33 | 9.00 | 0.79 | 12.00 | 4.02 | 2.94 |
| 13 | $Z_1$ | 5.00 | 1.00 | 9.00 | $AgNO_3$ | 0.16 | 9.00 | 0.68 | 12.00 | 4.23 | 2.54 |
| 14 | $Z_3$ | 5.00 | 1.00 | 5.00 | $AgNO_3$ | 0.16 | 9.00 | 0.68 | 7.00 | 4.23 | 2.54 |

TABLE 4

| Exp. No. | Carrier Type | W (g) | $CuSO_4$ and $NiAc_2$ mixed solution $W_{NiAc_2.4H_2O}$ (g) | $W_{CuSO_4.5H_2O}$ (g) | $W_{H_2O}$ (g) | $AgNO_3$ Solution $W_{AgNO_3}$ (g) | $W_{H_2O}$ (g) | $KBH_4$ solution $W_{KBH_4}$ (g) | $W_{H_2O}$ (g) | Initial atomic ratio Ni/M | Initial atomic ratio B/(Ni + M) |
|---|---|---|---|---|---|---|---|---|---|---|---|
| 15 | $Z_3$ | 5.00 | 1.00 | 0.06 | 5.00 | 0.04 | 5.00 | 0.50 | 7.00 | 8.41 | 2.06 |
| 16 | $Z_3$ | 5.00 | 1.00 | 0.06 | 5.00 | 0.02 | 5.00 | 0.50 | 7.00 | 11.19 | 2.12 |
| 17 | $Z_3$ | 5.00 | 1.00 | 0.12 | 5.00 | 0.04 | 5.00 | 0.50 | 7.00 | 5.59 | 1.96 |
| 18 | $Z_3$ | 5.00 | 1.00 | 0.06 | 5.00 | 0.16 | 5.00 | 0.70 | 7.00 | 3.38 | 2.49 |
| 19 | $Z_3$ | 5.00 | 1.00 | 0.12 | 5.00 | 0.16 | 5.00 | 0.70 | 7.00 | 2.81 | 2.38 |
| 20 | $Z_3$ | 5.00 | 2.24 | 0.24 | 5.00 | 0.16 | 5.00 | 1.10 | 7.00 | 2.10 | 3.44 |

TABLE 5

| Exp. No. | Carrier Type | W (g) | $NiAc_2$ Solution $W_{NiAc_2.4H_2O}$ (g) | $W_{H_2O}$ (g) | Solution of metal additive salt M salt | $W_M$ (g) | $W_{H_2O}$ (g) | $KBH_4$ solution $W_{KBH_4}$ (g) | $W_{H_2O}$ (g) | Initial atomic ratio Ni/M | Initial atomic ratio B/(Ni + M) |
|---|---|---|---|---|---|---|---|---|---|---|---|
| 21 | $Z_1$ | 5.00 | 1.00 | 9.00 | $Na_2MoO_4.2H_2O$ | 0.25 | 9.00 | 0.79 | 12.00 | 3.89 | 2.89 |
| 22 | $Z_1$ | 5.00 | 1.00 | 9.00 | $Na_2WO_4.2H_2O$ | 0.33 | 9.00 | 0.79 | 12.00 | 4.02 | 2.94 |

TABLE 6

| Exp. No. | Catal. No. | Content of Ni, B and M in catalyst (wt %) | atomic ratio (Ni + M)/B | atomic ratio Ni/M | Surface area (m²/g) |
|---|---|---|---|---|---|
| 1 | C1 | Ni 3.64; Cu 1.18; B 0.22 | 3.76 | 3.39 | 356 |
| 2 | C2 | Ni 0.37; Fe 1.09; B 0.17 | 5.25 | 3.20 | 358 |
| 3 | C3 | Ni 3.57; Co 0.89; B 0.24 | 3.35 | 4.13 | 362 |
| 4 | C4 | Ni 3.10; Mn 0.89; B 0.14 | 5.25 | 3.20 | 371 |
| 5 | C5 | Ni 2.79; Zn 1.80; B 0.13 | 6.14 | 1.77 | 329 |
| 6 | C6 | Ni 3.49; Mo 1.93; B 0.15 | 5.67 | 3.05 | 357 |

TABLE 6-continued

| Exp. No. | Catal. No. | Content of Ni, B and M in catalyst (wt %) | atomic ratio (Ni + M)/B | atomic ratio Ni/M | Surface area (m²/g) |
|---|---|---|---|---|---|
| 7 | C7 | Ni 3.16; Cu 1.12; B 0.38 | 2.03 | 2.94 | 451 |
| 8 | C8 | Ni 3.65; Cu 0.95; B 0.30 | 2.85 | 3.93 | 131 |
| 9 | C9 | Ni 4.17; Zn 1.36; B 0.34 | 2.85 | 3.63 | 146 |
| 10 | C10 | Ni 3.79; Cu 1.13; B 0.23 | 4.56 | 3.44 | 165 |
| 11 | C11 | Ni 3.58; Mo 1.91; B 0.17 | 5.25 | 3.00 | 359 |
| 12 | C12 | Ni 3.50; W 2.50; B 0.17 | 4.56 | 4.47 | 320 |
| 13 | C13 | Ni 4.17; Ag 2.22; B 0.24 | 4.00 | 3.44 | 315 |
| 14 | C14 | Ni 4.04; Ag 1.22; B 0.23 | 3.76 | 6.18 | 140 |
| 15 | C15 | Ni 3.81; Cu 0.24; Ag 0.45; B 0.40 | 1.94 | 8.43 | 131 |
| 16 | C16 | Ni 3.99; Cu 0.26; Ag 0.23; B 0.38 | 2.13 | 10.33 | 130 |
| 17 | C17 | Ni 3.93; Cu 0.56; Ag 0.45; B 0.42 | 2.03 | 5.09 | 138 |
| 18 | C18 | Ni 4.12; Cu 0.28; Ag 1.79; B 0.38 | 2.57 | 3.50 | 157 |
| 19 | C19 | Ni 3.84; Cu 0.55; Ag 1.79; B 0.39 | 2.57 | 2.60 | 156 |
| 20 | C20 | Ni 7.42; Cu 0.90; Ag 1.79; B 1.19 | 1.44 | 3.91 | 165 |
| 21 | C21 | Ni 3.09; Mo 1.21; B 0.14 | 4.88 | 4.19 | 364 |
| 22 | C22 | Ni 2.93; W 0.52; B 0.14 | 4.00 | 19.00 | 370 |

Examples 23–24

Described below is the preparation of catalysts 23–24 according to the present invention.

(1) Carriers

Carrier 5 (No. $Z_5$) is amorphous $SiO_2$ available from Shanghai Silicate Institute, China. Carrier 6 (No. $Z_6$) is $\alpha$-$Al_2O_3$. Their surface area and pore volume as well as crystalline phases are listed in Table 7.

TABLE 7

| Carrier No. | Type of carriers | Surface area (m²/g) | Pore volume (ml/g) | Crystalline phase |
|---|---|---|---|---|
| $Z_5$ | $SiO_2$ | 180 | 0.89 | amorphous |
| $Z_6$ | $Al_2O_3$ | 18.6 | 0.072 | $\alpha$ |

Figure 4:
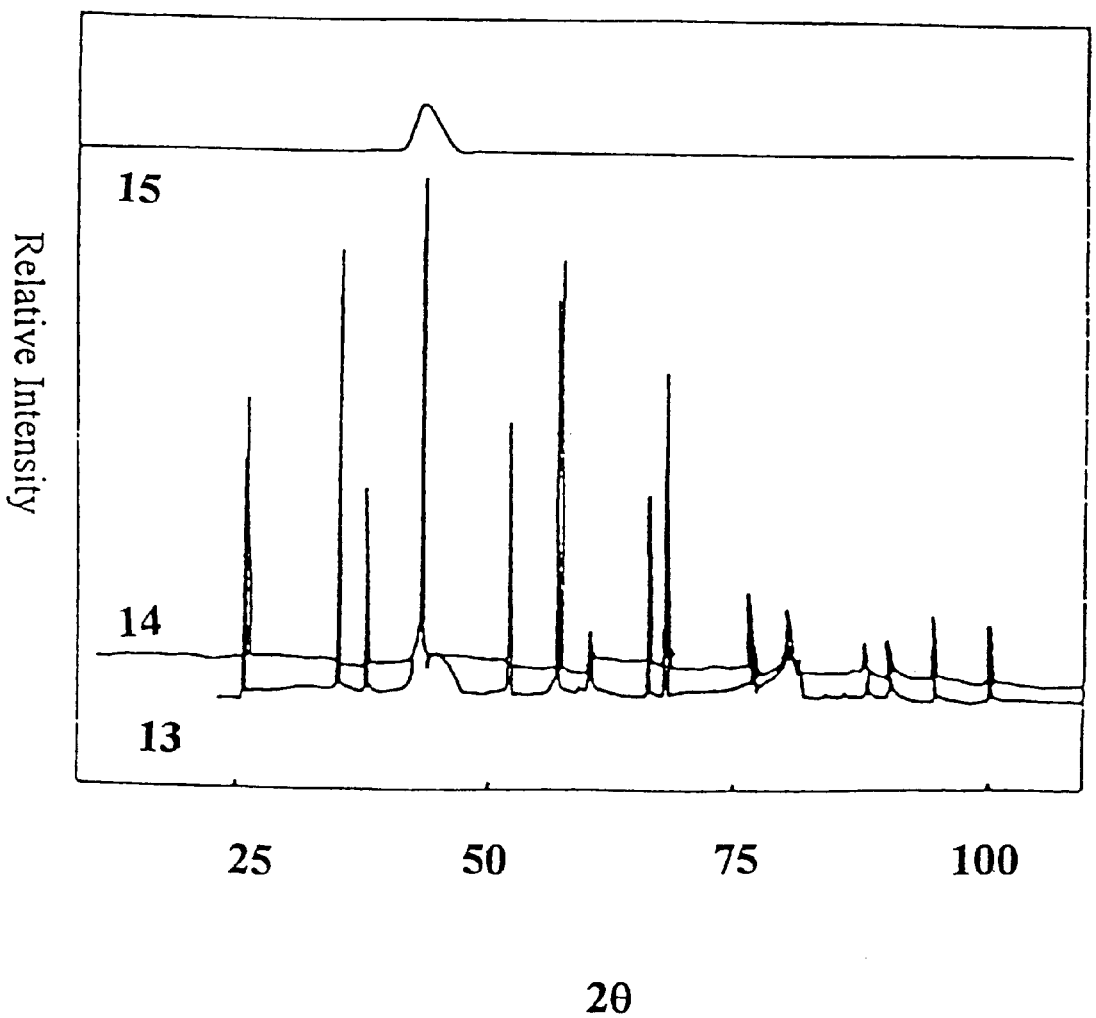
FIG. 4 shows the XRD patterns of the amorphous alloy catalysts according to the present invention using $\alpha$-$Al_2O_3$ as the carrier.

(2) Catalyst Preparation (a) The amounts of each of the above mentioned carriers $Z_5$ and $Z_6$ listed in Table 8 are dried at 120° C. The amounts of $NiCl_2$ and $CoCl_2$ listed in Table 8 are dissolved in the appropriate amount of distilled water, also listed in Table 8, to prepare the mixed $NiCl_2$ and $CoCl_2$ solution, which is then used for immersing the above carriers, $Z_5$ and $Z_6$. After the impregnated carriers are dried at 120° C., the $KBH_4$ aqueous solution prepared from the amounts of $KBH_4$ and water listed in Table 8, is added dropwise to the carriers. After the reaction is completed, which is indicated when no more significant quantitites of $H_2$ are released, the resulting solid products are washed with distilled water until free from acidic ions. These resulting catalysts according to the present invention are numbered as $C_{23}$ and $C_{24}$, corresponding to experiment numbers 23 and 24 in Table 8. Table 8 lists the quantities of all the materials used during the preparation. The contents of B, Ni and metal additive (Co) and the surface area of the catalysts of $C_{23}$ and $C_{24}$ are given in Table 9. The XRD pattern corresponding to catalyst $C_{23}$ is shown in FIG. 1(1). The XRD pattern corresponding to catalyst $C_{24}$ is shown in FIG. 4(13). FIG. 4(14) presents the XRD pattern corresponding to the $\alpha$-$Al_2O_3$ carrier, and FIG. 4(15) is the XRD pattern of the catalyst $C_{24}$ after subtracting the background of $\alpha$-$Al_2O_3$.

TABLE 8

| | Carrier | | Mixed solution | | | KBH₄ solution | | Initial | Initial |
|---|---|---|---|---|---|---|---|---|---|
| Exp. No. | Type | W (g) | $W_{NiCl_2}$ (g) | $W_{CoCl_2}$ (g) | $W_{H_2O}$ (g) | $C_{KBH_4}$ mol/l | Volume used (ml) | Atomic ratio Ni/M | atomic ratio B/(Ni + M) |
| 23 | $Z_5$ | 10 | 4.4 | 4.4 | 50 | 1 | 100 | 1.00 | 1.47 |
| 24 | $Z_6$ | 10 | 4.4 | 4.4 | 50 | 1 | 100 | 1.00 | 1.47 |

TABLE 9

| Exp. No. | Catal. No. | Contents of Ni, B and Co in the catalyst (wt %) | atomic ratio (Ni + Co)/B | Atomic ratio Ni/Co | Surface area m²/g |
|---|---|---|---|---|---|
| 23 | $C_{23}$ | Ni 10.3; Co 10.1; B 1.0 | 3.75 | 1.02 | 129 |
| 24 | $C_{24}$ | Ni 6.1; Co 7.1; B 0.77 | 3.15 | 0.86 | 15 |

Examples 25–32

The preparation of the catalysts $C_{25}$–$C_{32}$ according to the present invention.

The amount of $Z_5$ carrier listed in Table 10 is dried at 120°. The listed weights of $NiCl_2$ and the chlorides of the metal additives from Table 10 are dissolved in the amount of distilled water from Table 10, to prepare the mixed solution containing $Ni^{2+}$ and the ions of a metal additive (M). This solution is then used for immersing the above carrier $Z_5$. After the immersion step, the carriers are dried at 120° C., and to the carriers are added dropwise a solution containing the amount of $KBH_4$ listed in Table 10. After the reaction is completed, which is indicated when no more significant amount of $H_2$ is released, the resulting solid products are washed with distilled water until it is free from acidic ions. The resulted catalysts according to the present invention are numbered as $C_{25}$ to $C_{32}$, corresponding to experiment numbers 25 to 32 from Table 10. Table 10 shows the quantities of all the materials used during the preparation. The contents of B, Ni and metal additives and the surface area of the catalysts $C_{25}$ to $C_{32}$ are given in Table 11. The XRD pattern corresponding to catalysts $C_{25}$ to $C_{32}$ are shown in FIG. 1(1).

$LaCl_3$ mixed solution, which is then used for immersing the above $Z_5$ carrier. After the immersion step, the carrier is dried at 120° C., and then the $KBH_4$ solution, prepared according to Table 12, is added dropwise to the carrier. After the reaction is completed, which is indicated when no more significant amount of $H_2$ is released, the resulting solid products are washed with distilled water until free from acidic ions. The resulted $Pd-La-B/SiO_2$ catalyst prepared according to the present invention is numbered as $C_{33}$, corresponding to experiment number 33 from Table 12. The

TABLE 10

| Exp. No. | Carrier | | Mixed salt solution | | | $KBH_4$ solution | | Initial atomic ratio Ni/M | Initial atomic ratio B/(Ni + M) |
|---|---|---|---|---|---|---|---|---|---|
| | Type | W (g) | $W_{NiCl_2}$ (g) | M salt $W_M$ (g) | $W_{H_2O}$ (g) | $W_{KBH_4}$ (g) | $W_{H_2O}$ (g) | | |
| 25 | $Z_5$ | 10 | 3.2 | $PdCl_2$ 0.4 | 40 | 5.4 | 100 | 10.95 | 3.72 |
| 26 | $Z_5$ | 10 | 3.2 | $RuCl_3$ 0.4 | 40 | 5.4 | 100 | 12.83 | 3.76 |
| 27 | $Z_5$ | 10 | 3.2 | $IrCl_4$ 0.7 | 40 | 5.4 | 100 | 11.79 | 3.73 |
| 28 | $Z_5$ | 10 | 4.3 | $CeCl_3$ 5.0 | 40 | 5.4 | 100 | 1.63 | 1.87 |
| 29 | $Z_5$ | 10 | 4.3 | $LaCl_3$ 5.0 | 40 | 5.4 | 100 | 1.63 | 1.87 |
| 30 | $Z_5$ | 10 | 4.3 | $SmCl_3$ 5.0 | 40 | 5.4 | 100 | 1.71 | 1.90 |
| 31 | $Z_5$ | 10 | 4.3 | $Nd(NO_3)_3$ 7.0 | 40 | 5.4 | 100 | 1.57 | 1.84 |
| 32 | $Z_5$ | 10 | 4.3 | $Gd(NO_3)_3$ 7.0 | 40 | 5.4 | 100 | 1.63 | 1.87 |

TABLE 11

| Exp. No. | Catal. No. | Contents of Ni, B and M in the catalyst (wt %) | atomic ratio (Ni + M)/B | atomic ratio Ni/M | Surface area $m^2/g$ |
|---|---|---|---|---|---|
| 25 | $C_{25}$ | Ni 10.10; Pd 1.81; B 0.64 | 3.19 | 10.11 | 137 |
| 26 | $C_{26}$ | Ni 10.0; Ru 1.68; B 0.64 | 3.16 | 10.25 | 146 |
| 27 | $C_{27}$ | Ni 10.10; Ir 3.3; B 0.65 | 3.15 | 10.02 | 135 |
| 28 | $C_{29}$ | Ni 10.20; Ce 24.30; B 1.18 | 3.18 | 1.00 | 125 |
| 29 | $C_{29}$ | Ni 10.20; La 24.00; B 1.18 | 3.17 | 1.00 | 125 |
| 30 | $C_{30}$ | Ni 10.30; Sm 26.0; B 1.19 | 3.16 | 1.02 | 128 |
| 31 | $C_{31}$ | Ni 10.20; Nd 25.00; B 1.18 | 3.18 | 1.00 | 122 |
| 32 | $C_{32}$ | Ni 10.40; Gd 27.30; B 1.19 | 3.19 | 1.02 | 122 |

Examples 33–34

The preparation of the catalysts $C_{33}$–$C_{34}$ according to the present invention.

The amount of $Z_5$ carrier listed in Tables 12 or 13 is dried at 120° C. The amounts of $PdCl_2$ and $LaCl_3$ listed in Table 12 are dissolved in distilled water to prepare the $PdCl_2$ and $Ru-Ce-B/SiO_2$ catalyst according to the present invention is numbered as $C_{34}$ which is prepared in the same way as that of $C_{33}$, but using $RuCl_3$ and $CeCl_3$ instead of $PdCl_2$ and $LaCl_3$. Tables 12 and 13 show the quantities of all the materials used during the preparations. The contents of B, Q and metal additives and the surface area of the catalysts $C_{33}$ and $C_{34}$ are given in Table 14. The XRD patterns corresponding to catalyst $C_{33}$ and $C_{34}$ are shown in FIG. 1(1).

TABLE 12

| Exp. No. | Carrier | | Mixed salt solution | | | $KBH_4$ solution | | Initial atomic ratio Pd/La | Initial atomic ratio B/(Pd + La) |
|---|---|---|---|---|---|---|---|---|---|
| | Type | W (g) | $W_{PdCl_2}$ (g) | $W_{LaCl_3}$ (g) | $W_{H_2O}$ (g) | $C_{KBH_4}$ (mol) | Volume used (ml) | | |
| 33 | $Z_5$ | 10 | 0.084 | 0.1 | 50 | 1.0 | 21 | 1.00 | 1.47 |

TABLE 13

| Exp. No. | Carrier Type | W (g) | Mixed salt solution $W_{RuCl_3}$ (g) | $W_{CeCl_3}$ (g) | $W_{H_2O}$ (g) | $KBH_4$ solution $C_{KBH_4}$ (mol) | Volume used (ml) | Initial atomic ratio Ru/Ce | Initial atomic ratio B/(Ru + Ce) |
|---|---|---|---|---|---|---|---|---|---|
| 34 | $Z_5$ | 10 | 1.6 | 1.9 | 50 | 1.0 | 200 | 1.00 | 1.47 |

TABLE 14

| Exp. No. | Catal. No. | Contents of Q (Pd or Ru), B and M in the catalyst (wt %) | atomic ratio (Q + M)/B | atomic ratio Q/M | Surface area $m^2g$ |
|---|---|---|---|---|---|
| 33 | $C_{33}$ | Pd 0.5; La 0.6; B 0.029 | 3.65 | 1.00 | 139 |
| 34 | $C_{34}$ | Ru 8.0; Ce 9.0; B 1.43 | 3.22 | 1.00 | 121 |

Comparative Example 1

Preparation of Ni-La-P amorphous alloy with high surface area as a comparative catalyst.

A Ni-La-P amorphous alloy with a high surface area (No. $C_{35}$) is prepared according to the conditions and the employed quantities of each component described in Example 6 of CN 1073126A. The contents are determined by ICP as follows: Ni 87.4 wt %, La 0.4 wt %, P 12.2 wt %. The surface area is determined as 91 $m^2/g$ according to the same method described in examples 1–22.

Comparative Example 2

Preparation of polycrystalline Ni catalyst as a comparative catalyst.

A polycrystalline Ni catalyst (No. $C_{36}$) is prepared according to the following steps: 5.0 g of $Z_1$ carrier is impregnated with 9.82 g of a nickel nitrate solution at the strength of 8.35 wt %. This sample is dried at 100° C. for 4 hours and further calcined at 500° C. for 3 hours. The sample is then reduced in an $H_2$ flow at 460° C. for 4 hours. The Ni-loading is determined as 5.0 wt % by ICP.

Comparative Example 3

Preparation of Supported Ni-B catalyst containing no metal additive (M) as a comparative catalyst.

A Supported Ni-B catalyst is prepared according to the following steps. Take 5.0 grams of the $Z_1$ carriers and dry them at 120° C. Dissolve 1.0 gram of $NiAc_2 \cdot 4H_2O$ and 0.54 gram of $KBH_4$ in 9.0 ml and 12.0 ml of distilled water, respectively, to prepare the $NiAc_2$ and $KBH_4$ solutions. The $Z_1$ carriers are then impregnated with the $NiAc_2$ solution. After being dried at 120° C., the $KBH_4$ solution is then added dropwise at room temperature to the Ni-containing carrier. The reduction reaction is initiated immediately with the evolution of large amounts of $H_2$ being observed. After the reaction is completed, which is indicated when no more significant amount of $H_2$ is released, the resulting solid product is washed with distilled water until it is free from acidic ions. The supported Ni-B catalyst obtained in the manner is numbered as $C_{37}$. The analysis of this catalyst as determined by ICP is as follows: Ni 3.97 wt %, B 0.22 wt %, and the Ni/B atomic ratio is 3.42. The surface area is determined to be 341 $m^2/g$ according to the same method as that used in examples 1–22.

Example 35–40

The following examples describe the thermal stability of the catalysts according to the present invention.

Samples weighing 5.0 mg of each of the catalysts $C_1$, $C_2$, $C_5$, $C_6$, $C_{12}$, and $C_{13}$ are analyzed. The highest crystallization temperatures (Tc), as determined by DSC on a Du Pont 2100 Thermal Analysis System in an $N_2$ flow at the ramp of 10° C./min, are shown in Table 15.

Comparative Example 4

This Comparative Example demonstrates that the catalysts of the present invention exhibit higher thermal stability than the corresponding ultra-fine Ni-B amorphous alloy.

The highest crystallization temperature (Tc) of the ultra-fine Ni-B amorphous alloy catalyst employed here is determined by Deng et al. in J. Catal. 150 (1994) 435 as shown in Table 15.

TABLE 15

| Example No. | Catalyst No. | Tc (° C.) | Metal additive (M) | Radius of M(Å) |
|---|---|---|---|---|
| 35 | $C_1$ | 351 | Cu | 1.27 |
| 36 | $C_2$ | 396 | Fe | 1.24 |
| 37 | $C_5$ | 411 | Zn | 1.39 |
| 38 | $C_6$ | 429 | Mo | 1.36 |
| 39 | $C_{12}$ | 430 | W | 1.36 |
| 40 | $C_{13}$ | 355 | Ag | 1.44 |
| Comp. Exp. 4 | Ultra-fine Ni-B | 341.4 | None | — |

The results in Table 15 demonstrate that the catalysts of the present invention exhibit higher thermal stability than that of the corresponding ultra-fine Ni-B amorphous alloy. All of their crystallization temperatures are higher than 351° C., which are at least 9.6° C. more than that of the ultra-fine Ni-B amorphous alloy. The results in Table 15 also demonstrate that when the metal additives form an amorphous alloy with Ni-B, their thermal stability increases with an increase in size of those metal additives. For example, the highest crystallization temperatures of Ni-B catalysts of the present invention with Zn, Mo, and W metal additives reach 411 to 430° C.

The following examples and comparative examples describe the uses and the reactivity of the catalysts of the present invention during hydrogenation of compounds having various unsaturated functional groups.

Examples 41–45

The use of the catalysts of the present invention during the selective hydrogenation of trace ethyne in ethylene.

Figure 5:
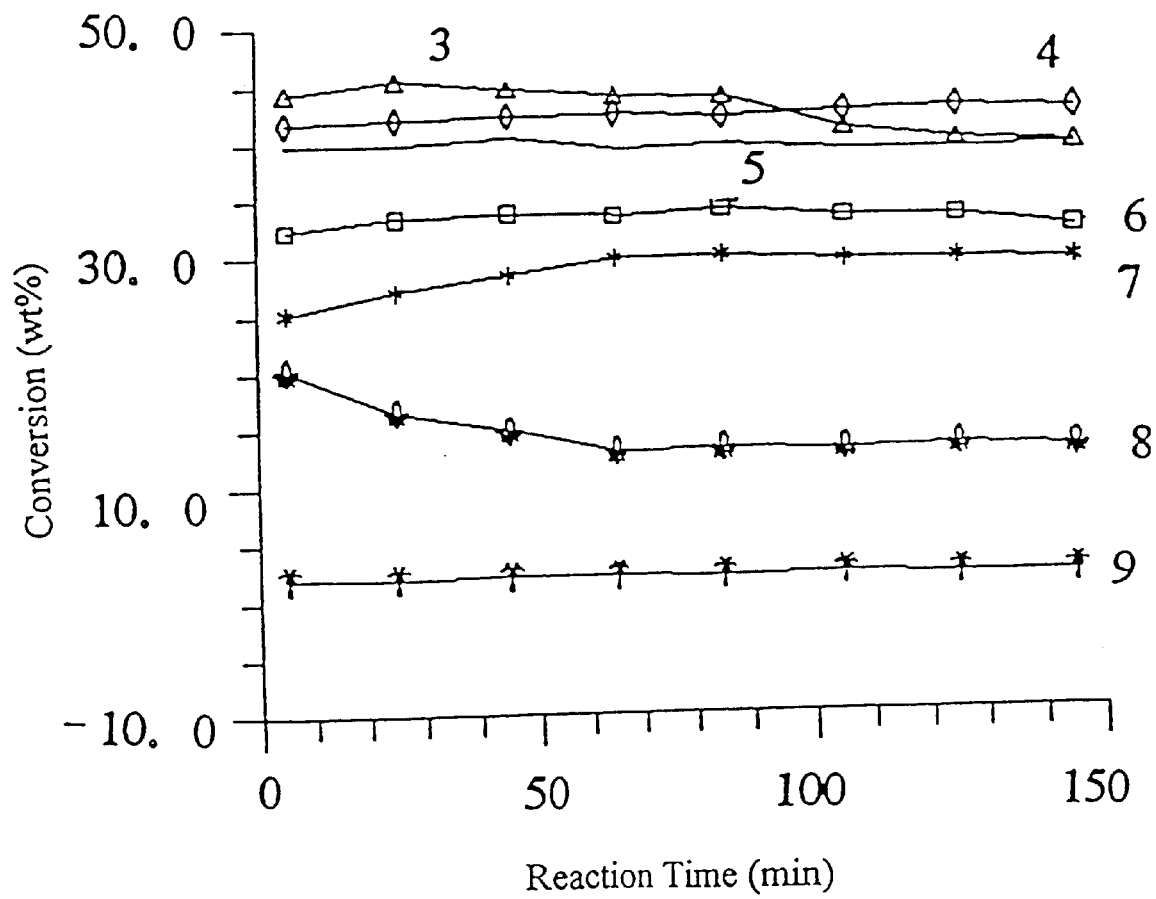
FIG. 5 shows the profile of ethyne conversion vs. reaction time during the selective hydrogenation of trace ethyne in ethylene using various catalysts.

Hydrogenation is carried out in a micro-reactor, with a 3 mm I.D. and 2000 mm in length. A 0.04 g sample of each of the catalysts $C_5$, $C_{13}$, $C_1$, $C_4$, and $C_{12}$, respectively, are employed. The composition of the feed gas is ethyne 1.65 mol %, ethylene 95.79 mol %, and hydrogen 2.56 mol %. The reaction conditions are T=110° C., P=10.0 MPa, gas space velocity=9000 hour$^{-1}$. The composition of the feed gas and products are analyzed by gas chromatography (GC). The profiles of ethyne conversion vs. reaction time are shown in FIG. 5 (3–7), corresponding to the catalysts $C_5$, $C_{13}$, $C_1$, $C_4$, and $C_{12}$, respectively.

Comparative Examples 5–6

The following comparative examples demonstrate that, during the selective hydrogenation of trace ethyne in ethylene, the reactivity of the catalysts of the present invention is obviously higher than that of the prior art catalysts reported thus far.

The reactor, raw materials, and reaction conditions are the same as those given in examples 41–45, except that the catalysts used are catalysts $C_{35}$ and $C_{36}$. The profiles of ethyne conversion vs. reaction time are shown in FIG. 5(8, 9).

Examples 46–48

The following examples also show that during the selective hydrogenation of trace ethyne in ethylene, the catalysts of the present invention exhibit high catalytic activity.

The reactor, raw materials, and reaction conditions are the same as those given in examples 41–45, except that the catalysts used are catalysts $C_{16}$, $C_{17}$, and $C_{18}$. The profiles of ethyne conversion vs. reaction time are shown in FIG. 6 (10–12).

Figure 6:
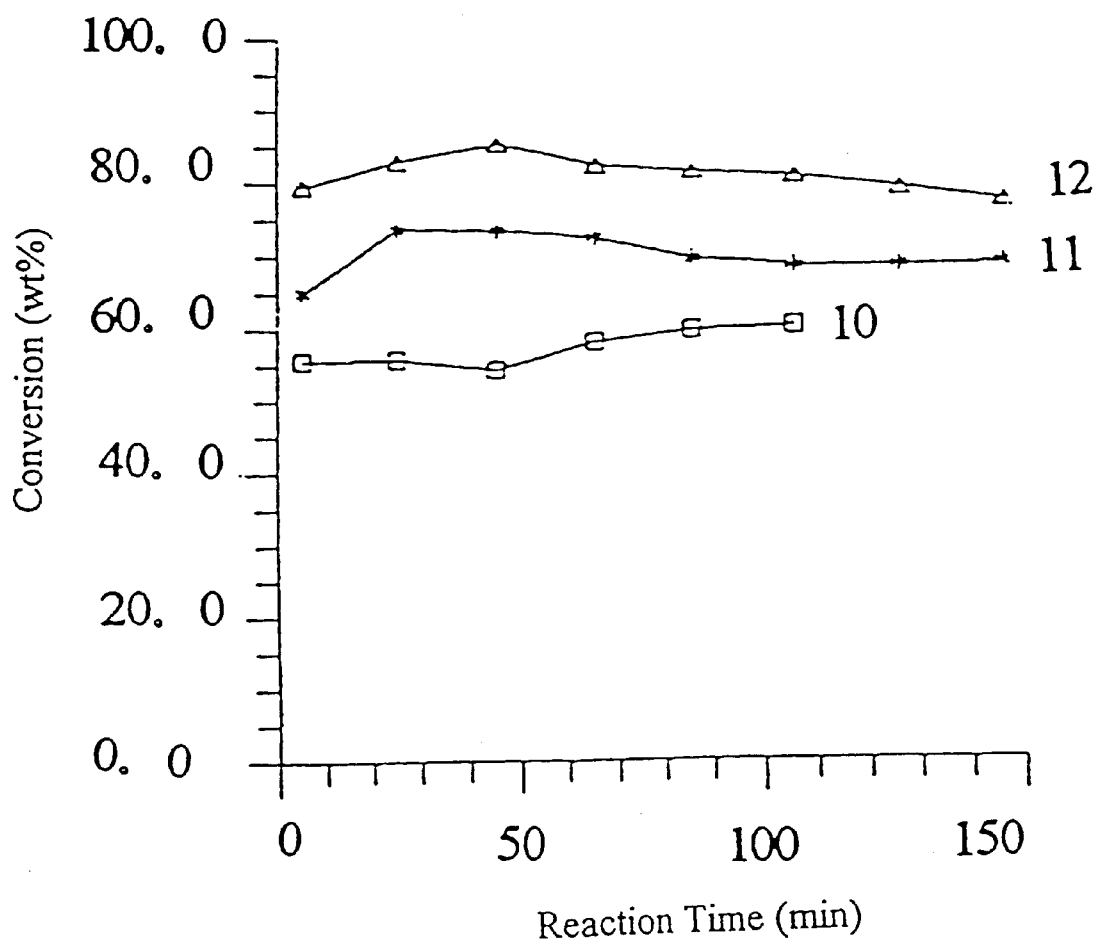
FIG. 6 shows the profile of ethyne conversion vs. reaction time during the selective hydrogenation of trace ethyne in ethylene using the amorphous alloy catalysts of the invention.

From the results in FIGS. 5 and 6, it can be seen that the catalysts of the present invention exhibit much higher activity than either the prior art amorphous alloy catalysts or the prior art polycrystalline Ni catalysts reported thus far.

Example 49

The use of the catalysts of the present invention for the hydrogenation of toluene into methylcyclohexane.

The reaction is performed in a 100 ml autoclave containing 50 ml of 20 wt % toluene, dissolved in cyclohexane, and 0.2 g of catalyst $C_1$. The autoclave is filled with $H_2$ and ventilated, and this procedure is repeated three time so as to replace all the air inside. The autoclave is then charged with $H_2$ up to a pressure of 4.0 MPa, and then heated up to 140° C. and maintained at this constant temperature during the reaction. The reaction is initiated by stirring the reaction mixture at a rate of 64 rpm. After the reaction proceeds for 1.0 hour, the products in the reaction mixture are analyzed by GC, the results of which are shown in Table 16.

Comparative Examples 7–8

These comparative examples demonstrate that during the hydrogenation of toluene into methylcyclohexane, the reactivity of the catalysts of the present invention are obviously higher than the prior art catalysts reported thus far.

The reactor, raw materials, and reaction conditions are the same as those given in example 49, except that the catalyst used is comparative catalyst $C_{35}$ or $C_{37}$, prepared according to comparative examples 1 or 3, respectively. The reaction results are shown in Table 16.

TABLE 16

| Example No. | Catalyst | Conversion (wt %) |
| --- | --- | --- |
| 49 | $C_1$ | 25.90 |
| Comparative example 7 | $C_{35}$ | 20.01 |
| Comparative example 8 | $C_{37}$ | 19.74 |

Example 50

The use of the catalysts of the present invention for the hydrogenation of styrene into ethylbenzene.

Hydrogenation is carried out in the same manner as that described in Example 49. The reaction conditions employed are 50 ml of styrene, 0.2 g of catalyst $C_3$, T=60° C., and reaction time=0.5 hour. The other steps of this example are the same as those provided in Example 49. The results of this example are shown in Table 17.

Comparative Examples 9–11

The following comparative examples demonstrate that, during the hydrogenation of styrene, the reactivities of the catalysts of the present invention are obviously higher than that of the prior art catalysts reported thus far.

The reactor, raw materials, and reaction conditions are the same as those provided in Example 50, except that the catalysts used are the comparative catalysts $C_{35}$, $C_{36}$, or $C_{37}$ prepared in Comparative Examples 1, 2, or 3. The reaction results are shown in Table 17.

TABLE 17

| Example No. | Catalyst | Conversion (wt %) |
| --- | --- | --- |
| 50 | $C_3$ | 18.63 |
| Comparative Example 9 | $C_{35}$ | 16.60 |
| Comparative Example 10 | $C_{36}$ | 0.10 |
| Comparative Example 11 | $C_{37}$ | 16.54 |

From the results in Tables 16 and 17 it can be seen that, for the hydrogenation of either toluene or styrene, the catalytic activity of all the catalysts of the present invention are much higher than those of the polycrystalline Ni catalysts. The activity of the catalysts of the present invention even exceeds that of the Ni-La-P amorphous alloy catalyst with high surface area, which has the highest reactivity among all the prior art amorphous alloy catalysts reported thus far. It is also demonstrated that the content of the catalytically active metal in the inventive Ni-M-B/carrier catalyst is present in a more finely divided state and more homogeneously distributed state than that in the Ni-La-P catalyst, since Ni-loading in the former catalyst is only 3.57–3.64 wt %, while Ni-loading in the Ni-La-P catalyst is very high, up to 87.4 wt %. These results indicate that the inventive Ni-M-B/carrier catalyst is a very effective catalyst having low Ni-loading, but displaying superiority over all the prior art catalysts. These results also indicate that the activity of the Ni-M-B/carrier catalyst of the present invention is higher than that of the supported Ni-B catalyst containing no metal additive (M).

Example 51

The use of the catalysts of the present invention for the hydrogenation of hexanedinitrile into hexanediamine.

Hydrogenation is carried in the same manner as that described in Example 49. Reaction conditions are as follows: 50 ml of ethanol solution containing 15 wt % of hexanedinitrile, 0.2 g of catalyst $C_{11}$, T=110° C., and reaction time=1 hour. The other steps of this example are the same as those given in Example 49. The results of this example are shown in Table 18.

TABLE 18

| Example No. | Catalyst | Conversion (%) |
|---|---|---|
| 51 | $C_{11}$ | 22.38 |

Examples 52–61

The use of the catalysts of the present invention for the hydrogenation of hexanedinitrile into hexanediamine.

Hydrogenation is performed in a 220 ml autoclave containing 10 ml of hexanedinitrile dissolved in 30 ml of ethanol, and in the presence of one of the catalysts $C_{23}$ to $C_{32}$. The autoclave is filled with $H_2$ and ventilated, and this procedure is repeated three time so as to replace all the air inside. The autoclave is then charged with $H_2$ up to a pressure of 4.0 MPa, heated up to 110° C., and maintained at this constant temperature during the reaction. The reaction is initiated by stirring the reaction mixture at a rate of 64 rpm. After the reaction has proceeded for 1.0 hour, the products in the reaction mixture are analyzed by GC, the results of which are shown in Table 19.

The selectivity of 1,6-hexanediamine ($S_{dia}$) is determined as follows $$S_{dia} = \frac{\text{weight of hexanedinitrile converted to 1,6-hexanediamine}}{\text{total weight of consumed hexanedinitrile}} \times 100\%$$

TABLE 19

| Example No. | Catalyst No. | Conversion of hexanedinitrile (wt %) | Selectivity of hexanediamine (%) |
|---|---|---|---|
| 52 | $C_{25}$ | 50.0 | 82.0 |
| 53 | $C_{26}$ | 44.0 | 90.0 |
| 54 | $C_{27}$ | 40.0 | 87.2 |
| 55 | $C_{28}$ | 50.8 | 68.7 |
| 56 | $C_{29}$ | 36.2 | 78.2 |
| 57 | $C_{30}$ | 56.5 | 89.2 |
| 58 | $C_{31}$ | 58.6 | 88.6 |
| 59 | $C_{32}$ | 60.4 | 88.5 |
| 60 | $C_{23}$ | 80.5 | 92.7 |
| 61 | $C_{24}$ | 68.2 | 90.7 |

Example 62

The use of the catalysts of the present invention for the hydrogenation of nitrobenzene into aniline.

Hydrogenation is carried in the same manner as that described in Example 49. Reaction conditions are as follows: 50 ml of a 2-propanolic solution containing 20 wt % of nitrobenzene, 0.2 g of catalyst $C_1$, T=89° C., and reaction time=1 hour. The other steps are the same as those provided in Example 49. The result of this example is shown in Table 20.

TABLE 20

| Example No. | Catalyst | Conversion of nitrobenzene (%) |
|---|---|---|
| 62 | $C_1$ | 2.54 |

Example 63–66

The use of the catalysts of the present invention during the hydrogenation of nitrobenzene to aniline.

Hydrogenation is carried in the same manner as that described in Example 49. Reaction conditions are as follows: 10 ml of nitrobenzene dissolved in 30 ml of an alcoholic solution, a 1.0 g sample of one of the catalysts $C_{25}$, $C_{26}$, $C_{27}$, and $C_{30}$ is employed for each run, T=89° C., P=1.0 MPa, and reaction time=1 hour. The other steps of these examples are the same as those provided in Example 49. The results of these examples are provided in Table 21.

The selectivity of aniline ($S_{ani}$) is determined as follows:

$$S_{ani} = \frac{\text{weight of nitrobenzene converted to aniline}}{\text{total weight of consumed nitrobenzene}} \times 100\%$$

TABLE 21

| Example No. | Catalyst No. | Conversion of nitrobenzene (wt %) | Selectivity of aniline (wt %) |
|---|---|---|---|
| 63 | $C_{25}$ | 100 | 100 |
| 64 | $C_{26}$ | 76.8 | 100 |
| 65 | $C_{27}$ | 82.5 | 100 |
| 66 | $C_{30}$ | 56.5 | 100 |

Example 67

The use of the catalysts of the present invention for the hydrogenation of cyclohexanone into cyclohexanol.

Hydrogenation is carried out in the same manner as that described in Example 49. Reaction conditions are as follows: 50 ml of cyclohexane solution containing 30 wt % of cyclohexanone, 0.2 g of catalyst $C_1$, T=95° C., reaction time=1 hour. The other steps of this example are the same as those provided in Example 49. The result of this example is shown in Table 22.

TABLE 22

| Example No. | Catalyst No. | Conversion of cyclohexanone (wt %) |
|---|---|---|
| 67 | $C_1$ | 1.02 |

Example 68

The use of the catalysts of the present invention for the hydrogenation of ethynylbenzene.

Hydrogenation is carried out in the same manner as that described in Example 49. Reaction conditions are as follows: 50 ml of cyclohexane solution containing 15 wt % of ethynylbenzene, 0.2 g catalyst $C_1$, T=22° C., reaction time= 0.5 hour. The other steps are the same as those provided in Example 49. The results of this example are shown in Table 23.

TABLE 23

| Example No. | Catalyst No. | Conversion of ethynylbenzene (wt %) | Selectivity to styrene (mol %) |
|---|---|---|---|
| 68 | $C_1$ | 7.32 | 100 |

The selectivity of styrene ($S_{styr}$) is determined as follows:

$$S_{styr} = \frac{\text{yield of styrene}}{\text{yield of styrene + yield of ethylbenzene}} \times 100\%$$

Examples 69–73

The use of the catalysts of the present invention for the hydrogenation of benzonitrile.

Hydrogenation is performed in a 220 ml autoclave containing 10 ml of benzonitrile dissolved in 30 ml of ethanol, and 1.0 g samples of one of the catalysts $C_{25}$, $C_{26}$, $C_{27}$, $C_{28}$, and $C_{30}$. The autoclave is filled with $H_2$ and then ventilated, and this procedure is repeated three time so as to replace all the air inside. The autoclave is then charged with $H_2$ up to a pressure of 4.0 MPa, heated up to 110° C., and maintained at that constant temperature throughout the reaction. Reaction is initiated by stirring the reaction mixture vigorously. The extent of the reaction is determined by monitoring the change in hydrogen pressure inside the autoclave every 10 minutes. These changes in hydrogen pressure are then converted into hydrogen uptake rates according to the ideal gas equation. The results of these examples are shown in Table 24.

TABLE 24

| Example No. | Catalyst No. | Hydrogen uptake rate (mmol $H_2$/hour · g Ni) |
|---|---|---|
| 69 | $C_{25}$ | 1976.5 |
| 70 | $C_{26}$ | 1865.4 |
| 71 | $C_{27}$ | 1802.4 |
| 72 | $C_{28}$ | 1965.6 |
| 73 | $C_{30}$ | 2000.2 |

Example 74–78

The use of the catalysts of the present invention for the hydrogenation of $CH_3CH=CHCOOH$.

Hydrogenation is carried out in the same manner as that described in Examples 69–73, except that the reaction solution is prepared by dissolving 10 g of $CH_3CH=CHCOOH$ in 30 ml of ethanol. The results of these examples are shown in Table 25.

TABLE 25

| Example No. | Catalyst No. | Hydrogen uptake rate (mmol $H_2$/hour · g Ni) |
|---|---|---|
| 74 | $C_{25}$ | 995.7 |
| 75 | $C_{26}$ | 898.6 |
| 76 | $C_{27}$ | 880.8 |
| 77 | $C_{28}$ | 765.6 |
| 78 | $C_{30}$ | 854.2 |

Examples 79–83

The use of the catalysts of the present invention for the hydrogenation of $CNCH_2CN$.

Hydrogenation is carried out in the same manner as that described in Examples 69–73, except that the reaction solution is prepared by dissolving 10 ml of $CNCH_2CN$ in 30 ml of ethanol. The results of these examples are shown in Table 26.

TABLE 26

| Example No. | Catalyst No. | Hydrogen uptake rate (mmol $H_2$/hour · g Ni) |
|---|---|---|
| 79 | $C_{25}$ | 3200.4 |
| 80 | $C_{26}$ | 3129.8 |
| 81 | $C_{27}$ | 2896.4 |
| 82 | $C_{28}$ | 2568.5 |
| 83 | $C_{30}$ | 3454.6 |

Example 84

The use of the catalysts of the present invention for the hydrogenation of 4-carboxyl-benzaldehyde (4CBA).

Hydrogenation is carried out batchwise in a 500 ml autoclave containing 160 ml of an aqueous solution containing 2000 ppm of 4CBA, 40 g of 4-carboxyl-benzoic acid, and 3.0 g of catalyst $C_{33}$. The autoclave is filled with $H_2$ and ventilated, and this procedure is repeated three times so as to replace all the air inside. The autoclave is then charged with $H_2$ to a pressure of 6.8 MPa, heated to 278° C., and maintained at this constant temperature throughout the reaction. Reaction is initiated by stirring the reaction mixture at rate of 120 rpm. After no additional $H_2$ consumption is observed, the products in the reaction mixture are analyzed by polargraphy, the result of which is shown in Table 27.

TABLE 27

| Example No. | Catalyst No. | Conversion (wt %) |
|---|---|---|
| 84 | $C_{33}$ | 94.7 |

Example 85

The use of the catalysts of the present invention during the hydrogenation of benzene into cyclohexadiene.

Hydrogenation is performed batchwise in a 500 ml autoclave containing 30 ml of benzene, 80 ml of distilled water, a small amount of $ZnSO_4$ additive, and 1.0 g of catalyst $C_{34}$. The autoclave is filled with $H_2$ and ventilated, and this procedure is repeated three time so as to replace all the air inside. The autoclave is charged with $H_2$ up to a pressure of 4.0 MPa, heated up to 150° C., and maintained at this constant temperature throughout the reaction. Reaction is initiated by stirring the reaction mixture at a rate of 120 rpm. After no additional $H_2$ consumption is observed, the products in the reaction mixture are analyzed by GC. The results of this example are shown in Table 28.

TABLE 28

| Example No. | Catalyst No. | Conversion (wt %) |
|---|---|---|
| 85 | $C_{34}$ | 38.4 |

We claim:

1. An amorphous alloy catalyst containing boron, characterized in that said catalyst is composed of a porous carrier, a Q-B amorphous alloy and a metal additive (M), the content of Q-B amorphous alloy together with said metal additive is from 0.1 to 60 wt %, based on the total weight of the catalyst, in which the atomic ratio (Q+M)/B is 0.5–10, and atomic ratio Q/M is 0.1–1000; Q represents a metal selected from group VIII and B represents boron; and said metal additive (M) refers to one or more metal elements which can be reduced to its/their elemental states from the corresponding salts by a solution containing $BH_4^-$ with the exception that M is not the one which is used as Q.

2. A catalyst according to claim 1, characterized in that said content of Q-B amorphous alloy together with metal additive (M) is from 0.1 to 40 wt %.

3. A catalyst according to claim 1, characterized in that said content of Q-B amorphous alloy together with metal additive (M) is from 0.1 to 30 wt %.

4. A catalyst according to claim 1, characterized in that said atomic ratio (Q+M)/B is 1–8, and said atomic ratio Q/M is from 0.5 to 100.

5. A catalyst according to claim 4, characterized in that said atomic ratio Q/M is from 0.5 to 25.

6. A catalyst according to claim 1, characterized in that said Q is selected from Ni, Fe, Co, Ru, Rh, Pd, Os, Ir or Pt.

7. A catalyst according to claim 6, characterized in that said Q is selected from Ni, Ru or Pd.

8. A catalyst according to claim 7, characterized in that said Q is Ni.

9. A catalyst according to claim 1, characterized in that said porous carrier is selected from porous inorganic oxides, active carbon, zeolite, molecular sieve or a mixture comprising two or more of them.

10. A catalyst according to claim 9, characterized in that said porous carrier is selected from silica or alumina.

11. A catalyst according to claim 1, characterized in that said metal additive is selected from one or several metal elements in group IVA, IB, IIB, IIIB, VIB, VIIB, and all the metal elements in group VIII except for the one which is used as Q.

12. A catalyst according to claim 11, characterized in that said metal additive (M) is one or more metal elements selected from the group comprising Fe, Co, Cu, Zn, Mn, Ag, Mo, W, Pd, Ru, Ir, La, Ce, Sm, Nd, Gd.

13. A catalyst according to claim 1, characterized in that the surface area of the catalyst is from 10 to 1000 $m^2/g$.

14. A catalyst according to claim 13, characterized in that the surface area of the catalyst is from 100 to 1000 $m^2/g$.

15. A process for preparation of the catalyst as claimed in claim 1, characterized in that the process comprises contacting a porous carrier containing Q and metal additive (M) with a solution containing $BH_4^-$ at a molar concentration of between 0.5–10 M, in a initial atomic ratio of B/(Q+M) being from 0.1 to 10 and a initial atomic ratio of Q/M in said porous carrier being from 0.1 to 80, at a temperature ranging from the melting point of the solution to 100° C.

16. A process according to claim 15, characterized in that said solution containing $BH_4^-$ is an aqueous solution containing $BH_4^-$, the precursor of $BH_4^-$ ions is selected from $KBH_4$, $NaBH_4$ or a mixture thereof.

17. A process according to claim 15, characterized in that said initial molar ratio of B/(Q+M) is from 1 to 4.

18. A process according to claim 15, characterized in that said initial molar ratio of Q/M in said porous carrier is from 0.5 to 20.

19. A process according to claim 15, characterized in that said Q is selected from Ni, Ru or Pd.

20. A process according to claim 19, characterized in that said Q is Ni.

21. A process according to claim 15, characterized in that said contacting is carried out by adding the solution containing $BH_4^-$ dropwise to the carrier containing Q and metal additive M, at a temperature ranging from room temperature to 50° C.

* * * * *